United States Patent [19]

Lapin et al.

[11] Patent Number: 5,969,159
[45] Date of Patent: Oct. 19, 1999

[54] SYNTHESIS OF CYCLOPENTYL 2-THIENYL KETONE TILETAMINE AND TILETAMINE ACID ADDITION SALTS SUCH AS TILETAMINE HYDROCHLORIDE

[75] Inventors: Yuri Aleksandrovich Lapin, West Lafayette; Ignacio H. Sanchez, Lafayette, both of Ind.

[73] Assignee: Great Lakes Chemical Corporation, West Lafayette, Ind.

[21] Appl. No.: 09/250,368

[22] Filed: Feb. 16, 1999

[51] Int. Cl.$^6$ .................................................. C07D 333/22
[52] U.S. Cl. .................................................. 549/76; 549/70
[58] Field of Search ........................................ 549/76, 70

[56] References Cited

U.S. PATENT DOCUMENTS

| | | | |
|---|---|---|---|
| 3,342,836 | 9/1967 | L'Italien | 549/76 |
| 3,522,273 | 7/1970 | Parcell | 260/332.3 |
| 4,761,486 | 8/1988 | Zeeh et al. | 549/9 |
| 5,034,400 | 7/1991 | Olney | 514/315 |
| 5,597,832 | 1/1997 | Michaelides et al. | 514/285 |
| 5,616,580 | 4/1997 | Olney | 514/226.2 |
| 5,648,087 | 7/1997 | Ovaert et al. | 424/423 |

OTHER PUBLICATIONS

Clerici, F., et al., "N'–Arylsulfonylamidines: Part 2. A New Synthesis of Ketones from N–Tosylamidines and Organolithium Compounds", *Synthesis* Nov. 1987, pp. 1025–1027.

Jur'ew, Yu K., et al., *ZH. Obshch–Khim* 26 (1956), pp. 3341–3344.

*Primary Examiner*—Deborah C. Lambkin
*Attorney, Agent, or Firm*—Marshall, O'Toole, Gerstein, Murray & Borun

[57] ABSTRACT

Solid, non-tin-containing catalysts can be used for the synthesis of cyclopentyl 2-thienyl ketone by the reaction of cyclopentanecarboxylic acid chloride and thiophene, while achieving new and unexpected yields. Aluminum trichloride is both cheaper than stannic chloride and it is easier to deal with as a waste stream. The successful use of graphite as a catalyst for the reaction of cyclopentanecarboxylic acid chloride and thiophene provides a mild and ecologically friendly method for carrying out the Friedel-Crafts reaction. A tiletamine-free base can be made from the cyclopentyl 2-thienyl ketone with a halide in the presence of a solvent for the cyclopentyl 2-thienyl ketone to form a halogenated cyclopentane 2-thienyl ketone; aminating the halogenated cyclopentane 2-thienyl ketone by reaction with an amine; and subjecting the reaction product to thermal rearrangement, in a suitable solvent, and at a sufficient temperature to form tiletamine free base. Each step for the formation of tiletamine free base can be accomplished using the same solvent, e.g., dichlorobenzene so that intermediates need not be isolated between reactions.

28 Claims, No Drawings

SYNTHESIS OF CYCLOPENTYL 2-THIENYL KETONE TILETAMINE AND TILETAMINE ACID ADDITION SALTS SUCH AS TILETAMINE HYDROCHLORIDE

BACKGROUND OF THE INVENTION

1. Field of the Invention

The present invention is directed to an improved method of making cyclopentyl 2-thienyl ketone, tiletamine and tiletamine acid addition salts, such as tiletamine hydrochloride.

2. Description of the Prior Art

U.S. Pat. No. 3,522,273 ('273) discloses a method of making tiletamine, or 2-amino-2-(2'-thienyl)cyclohexanone, and tiletamine acid addition salts, such as the hydrochloride.

As disclosed in the '273 patent, there are two routes to the synthesis of tiletamine hydrochloride, based on cyclopentyl 2-thienyl ketone (Scheme 1) or tetrahydro-2-pyranyl ether of cyclopentanone cyanohydrin (Scheme 2) as starting compounds, as follows:

Scheme 1:

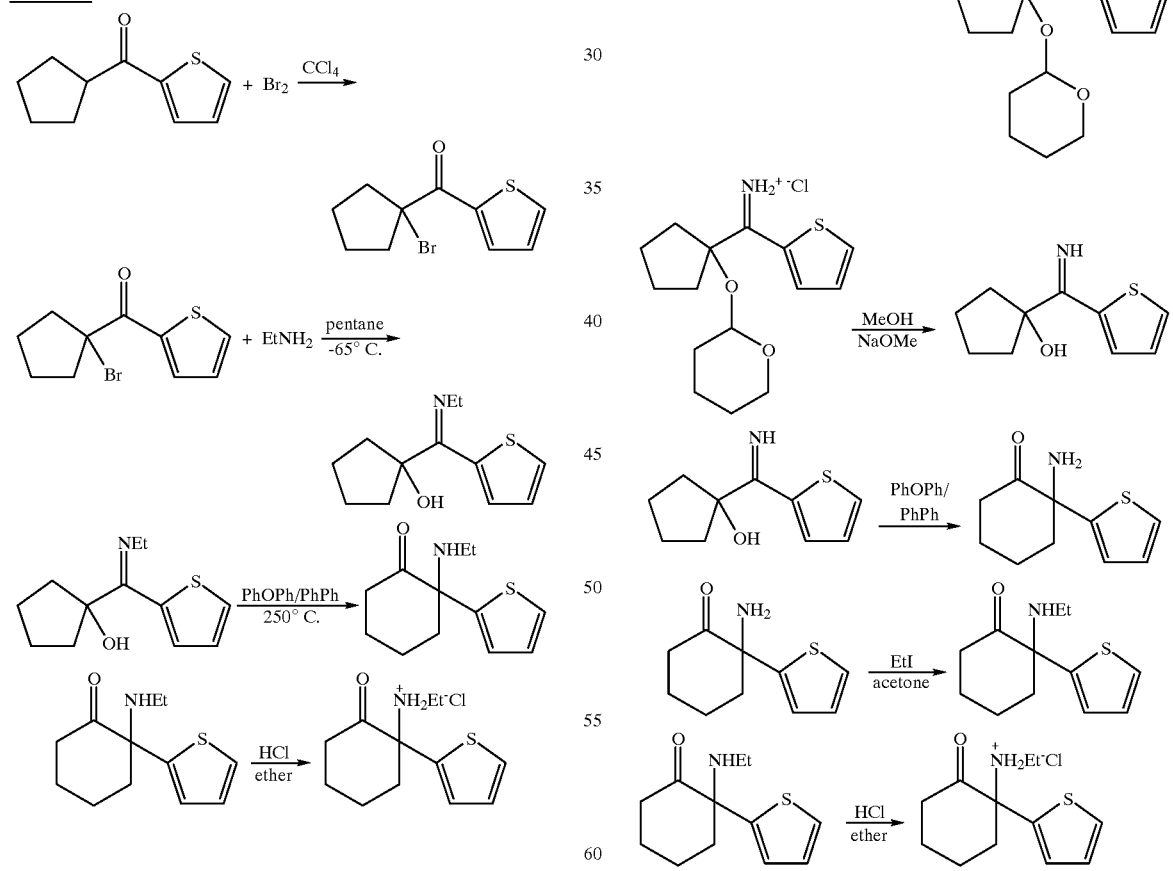

Scheme 2:

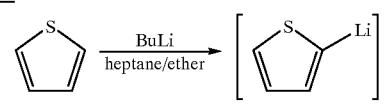

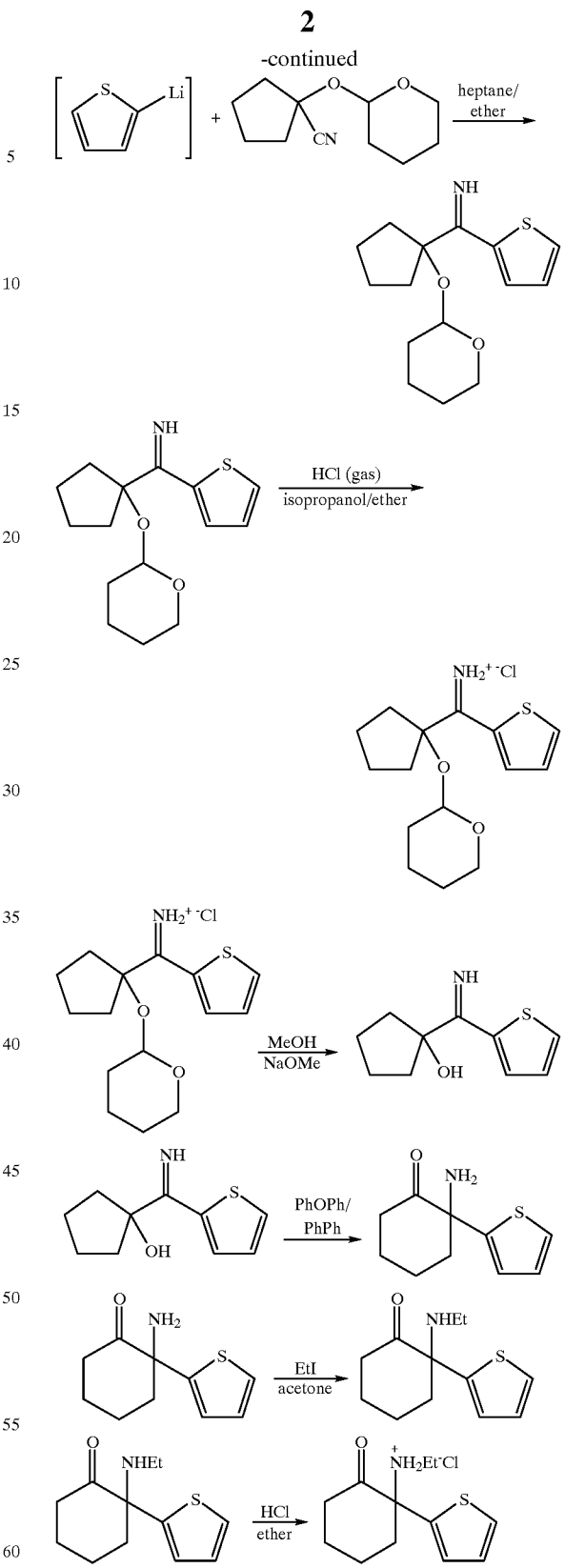

Due to availability of the starting compound, lower number of separate steps, lower raw material and operational costs, Scheme 1 is more promising than Scheme 2. However, both Schemes have several shortcomings. First, each step of the synthesis requires a different solvent. Multiple solvents complicate the post-reaction work-up, isolation and solvent recovery steps, and add significantly to the manufacturing cost of the process. In addition, solvents such as carbon tetrachloride and ether are restricted solvents. Moreover, ether is difficult to recover industrially and highly flammable. Second, the processes typically call for multiple isolations and purifications of the intermediates, which substantially effects the operational cost of commercial manufacture.

Cyclopentyl 2-thienyl ketone has been prepared by the Friedel-Crafts reaction of thiophene with initially preformed cyclopentanecarboxylic acid chloride (Scheme 3), as disclosed in U.S. Pat. No. 5,597,832 or with tetracyclopentylcarboxysilane (Scheme 4), Jur'ew, Yu K., et al. *Zh. Obshch-Khim.*; 26, 1956, 3341–3343:

Scheme 3 (Example 33a of 5,597,832):

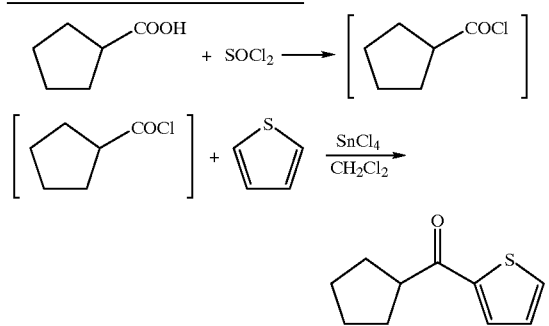

Scheme 4:

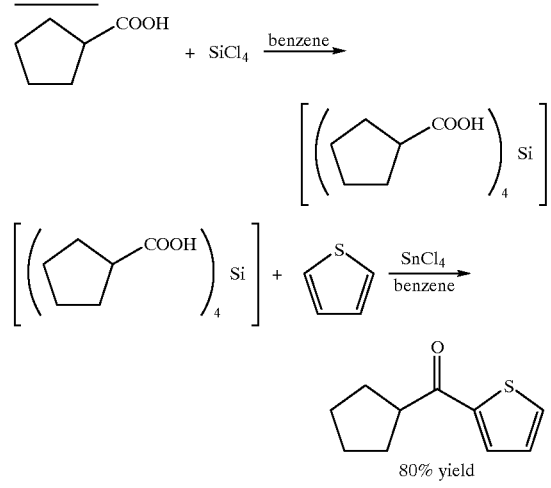

80% yield

Both Schemes 3 and 4 have the same major shortcoming—stannic chloride is used as a catalyst for the Friedel-Crafts reaction. In addition to its cost, stannic chloride introduces a heavy metal contamination to the process waste stream which is a major problem during manufacture.

It is also known, that cyclopentyl 2-thienyl ketone can be prepared from N'-tosylcyclopentylamidine by reaction with 2-thienyl lithium (Scheme 5), see Clerici, F. et al. *Synthesis,* 11, 1987, 1025–1027:

Scheme 5:

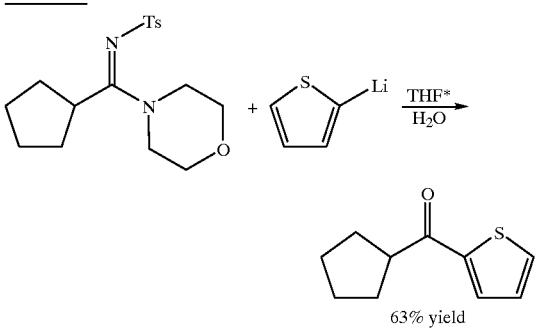

63% yield

*tetrahydrofuran

This Scheme 5 approach has some scientific interest, but is not desirable from a commercial production standpoint.

In accordance with the present invention, we have discovered alternatives to the original acylation routes to synthesize cyclopentyl 2-thienyl ketone. It has been found that cyclopentanecarboxylic acid chloride can be reacted with thiophene using a solid catalyst, other than stannic chloride, at unexpectedly high yields, to avoid the stannic chloride (heavy metal) waste stream contamination. In accordance with a preferred embodiment of the present invention, aluminum trichloride or graphite are the catalysts of choice for the Friedel-Crafts reaction of cyclopentanecarboxylic acid chloride and thiophene (Scheme 6(b) and (c)):

Scheme 6 (Non-tin-containing Catalytic Friedel-Crafts Reaction)

The synthesis of cyclopentanecarboxylic acid chloride, in accordance with the following reaction (a), can be achieved by reacting cyclopentanecarboxylic acid with thionyl chloride, with or without a solvent. In accordance with a preferred embodiment of the present invention, the same solvent, preferably o-dichlorobenzene, can be used for reaction (a) and the following reactions (b) or (c) so that solvent removal is unnecessary between reactions for isolation of intermediates, e.g., after reaction (a).

(a)

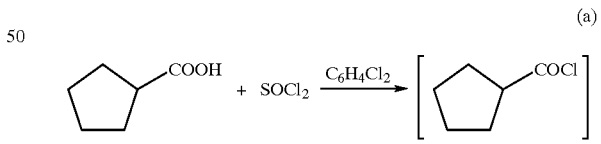

As shown in the prior art method of Scheme 3, the prior art reaction requires a tin-containing catalyst, such as stannic chloride, and methylene chloride as a solvent for the reaction of cyclopentanecarboxylic acid chloride with thiophene to form cyclopentyl 2-thienyl ketone. In accordance with an important feature of the present invention, it has been found that other, solid, less waste stream-polluting catalysts can be used for the synthesis of cyclopentyl 2-thienyl ketone by the reaction of cyclopentanecarboxylic acid chloride and thiophene, while achieving new and unexpected yields, as shown in the following reactions (b) and (c):

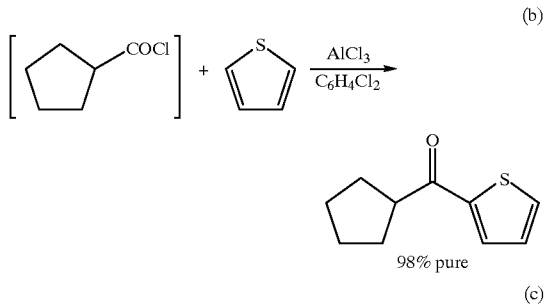

(b)

98% pure (c)

84% pure

Aluminum trichloride is both cheaper than stannic chloride and it is easier to deal with as a waste stream. The successful use of graphite as a catalyst for the reaction of cyclopentanecarboxylic acid chloride and thiophene provides a mild and ecologically friendly method for carrying out the Friedel-Crafts reaction. The additional advantage of such an approach includes easier work up, which only requires a simple filtration of the solid catalyst for isolation of the cyclopentyl 2-thienyl ketone reaction product.

The ortho-dichlorobenzene ($C_6H_4Cl_2$) solvent used in the reaction (a) of cyclopentanecarboxylic acid and thionyl chloride ($SOCl_2$), and in reaction (b) or (c), was also used in the following reaction Schemes 7 and 8. However, other solvents can be used in accordance with the present invention, such as chlorobenzene or dichloroethane as well. Any non-reactive hydrocarbon solvent or chlorinated hydrocarbon solvent is suitable for the reactions of Schemes 6–9 described herein. Higher boiling solvents, having a boiling point of at least about 100° C., are preferred so that the thermal rearrangement reaction of Scheme 9 can be performed at the solvent reflux temperature, at a temperature of at least 100° C., in a commercially acceptable time period. The o-dichlorobenzene is most advantageous since it forms an azeotropic mixture with water for stripping off the water with the o-dichlorobenzene to achieve the most economical drying of intermediates and product. Further, by using the same solvent in sequential steps of the synthesis, it is not necessary to isolate intermediate reaction products from the solvent and unreacted reactants before proceeding with the next sequential step of the process—making the process extremely more commercially viable. The amount of solvent, e.g., o-dichlorobenzene, used in the reactions should be sufficient to dissolve solid reactants. Reaction initiators, such as dimethylformamide, can be added to speed the reaction(s), but are not essential for achieving reactions with excellent yields.

Halogenation (bromination) of the crude cyclopentyl 2-thienyl ketone in o-dichlorobenzene solution at room temperature gave the corresponding α-halogenated ketone with a high purity, usually 97–99% by GC, area % analysis (Scheme 7).

Scheme 7 (bromination):

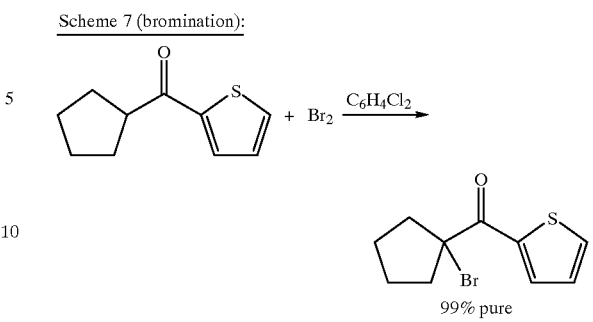

99% pure

A work up procedure after the bromination step is a simple evaporation of the solvent, which can be collected and recycled to any step of the process. Evaporation of the o-dichlorobenzene removes residual hydrogen bromide as well. A crude material, without any purification, was carried through directly to the next amination step. A 75% wt/wt solution of α-bromoketone in o-dichlorobenzene was used to prevent solidification of the starting material during amine addition. The amination reaction resulted in 96% pure (GC, area % analysis) product (Scheme 8).

Scheme 8 (amination):

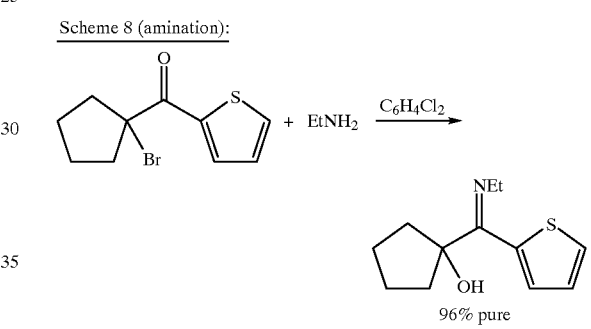

96% pure

An excess of ethylamine, used in the reaction, was evaporated from the reaction mixture under mild vacuum, and the ethylamine was recovered and recycled. An ethylamine hydrobromide salt by-product was washed out with water. A solution of crude 1-hydroxycyclopentyl 2'-thienyl N-ethyl ketimine in o-dichlorobenzene was refluxed for 1.5 hours at a temperature of at least about 100° C., preferably about 180° C. to about 230° C., e.g. 220° C. to 225° C., to produce 90% pure (GC, area % analysis) tiletamine free base by the thermal rearrangement reaction shown in Scheme 9.

Scheme 9 (thermal rearrangement):

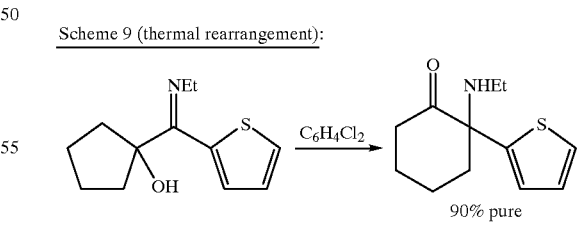

90% pure

The single solvent strategy until this point, as shown in Schemes 6, 7, 8 and 9, and the capability of transferring a crude reaction mixture through the above-described steps without isolation of the intermediates resulted in up to 70% yield (based on cyclopentanecarboxylic acid) of tiletamine free base. The conversion of tiletamine to its hydrochloride salt in o-dichlorobenzene at this stage allows for the use of only a single solvent throughout the entire process.

However, a reaction of hydrogen chloride gas with tiletamine in o-dichlorobenzene was found to result in conversion of only about 39% of the available free base to the hydrochloride salt. Therefore, a different solvent was used for the final reaction to obtain higher conversion. In the prior art method diethyl ether was the solvent of choice for this step, but diethyl ether is flammable and very difficult to handle. We have found that the use of n-butyl ether or t-butyl methyl ether and HCl gas result in the complete conversion of tiletamine to the corresponding hydrochloride salt, as shown in the acid addition salt reaction of Scheme 10.

Scheme 10 (acid addition salt reaction):

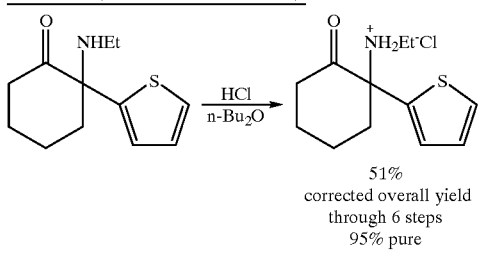

51%
corrected overall yield
through 6 steps
95% pure

As described above, synthesis of cyclopentyl 2-thienyl ketone, tiletamine and tiletamine acid addition salts has the following distinct advantages:

1. Tiletamine and its hydrochloride salt are produced with high yield.
2. The multi-solvent process can be replaced by a procedure, employing only one solvent for the synthesis of tiletamine free base—two solvents for good yields of tiletamine acid addition salts, involving a second solvent only at the acid addition salt step of the process.
3. A crude reaction mixture can be carried through six steps while avoiding complicated work ups, isolations, and purifications of the intermediates.

EXAMPLES

Example 1

Cyclopentanecarboxylic Acid Chloride Synthesis

Thionyl chloride (28.14 g, 236 mmol., 1.09 equivs.) was added during 20 min to a stirred solution of cyclopentanecarboxylic acid (25 g, 219 mmol) and dimethylformamide (0.1 mL) in o-dichlorobenzene (ODCB) (50 mL) at 30° C. The reaction was heated at 50° C. for a further 2.5 hours then analyzed by GC area % analysis and found to be complete. No work up of the reaction mixture or isolation of cyclopentanecarboxylic acid chloride was required. The crude solution of cyclopentanecarboxylic acid chloride was carried through directly to the next step, assuming a 100% yield.

Example 2

Cyclopentyl 2-thienyl Ketone Synthesis
a. Aluminum Chloride as a Catalyst

Thiophene (18.43 g, 219 mmol) was added to the cyclopentanecarboxylic acid chloride (219 mmol assumed) solution (the crude reaction mixture from Example 1). Aluminum chloride (29.2 g, 219 mmol) was added to the stirred reaction mixture over 1 hour at 0° C. The reaction mixture was then allowed to warm up to room temperature. After 1 hour at room temperature, the mixture was quenched by adding 10% hydrochloric acid (42 mL). Cooling was used to keep the temperature below 30° C. to minimize the formation of by-products. The mixture was stirred for 1 hour. The organic layer was separated and the aqueous phase was extracted with o-dichlorobenzene. The organic layers were combined and washed with water. The crude cyclopentyl-2-thienyl ketone exhibited a 98% purity (GC, area % analysis). The reaction mixture was azeotropically dried by stripping a small portion of the o-diclorobenzene solvent under vacuum. The crude cyclopentyl 2-thienyl ketone solution was then used without purification, for the bromination step of Example 3.
b. Graphite as a Catalyst Graphite (6.0 g) was added to a mixture of thiophene (2.46 g, 29.2 mmol) and cyclopentanecarboxylic acid chloride (29.2 mmol assumed—the crude mixture from Example 1) in 50 mL of o-dichlorobenzene. The mixture was heated and kept at 80° C. for 1.5 hours. It is understood that lower temperatures can be used for longer times, or higher temperatures for shorter times while achieving good yields of cyclopentyl 2-thienyl ketone. After cooling down to room temperature, graphite was removed by filtration and washed with a small portion of the o-dichlorobenzene solvent. The product mixture was subjected to mild heating to remove the residual amount of HCl. The crude cyclopentyl 2-thienyl ketone of 84% purity (GC, area % analysis) was transferred, without purification, to the bromination step of Example 3.

Example 3

1-Bromocyclopentyl 2'-thienyl Ketone

Bromine (74.9 g, 468.66 mmol) was added for 30 min to a stirred solution of crude cyclopentyl 2-thienyl ketone (438 mmol assumed, a reaction mixture from Examples 2a or 2b) in o-dichlorobenzene at room temperature. The reaction mixture was stirred for a further hour and concentrated under vacuum to leave an oily product, which was 99% pure (GC, area % analysis) 1-bromocyclopentyl 2'-thienyl ketone.

Example 4

1-Hydroxycyclopentyl 2'-thienyl N-ethyl Ketimine

Ethylamine (8.2 g, 181.35 mmol, 4.7 equivs.) was condensed in a flask, which had an attached dry ice condenser. The crude α-bromoketone (38.58 mmol assumed) from Example 3 was then added slowly over 1 hour, keeping the temperature at approximately 0° C. After a further 2 hours of stirring, the reaction mixture was allowed to warm to room temperature for another 2 hours. The remaining ethylamine was evaporated under mild vacuum. An excess of ethylamine, removed from the reaction mixture, was recovered and recycled. The reaction mixture was diluted with 25 mL of o-dichlorobenzene and quickly washed with cool water to remove the ethylamine hydrobromide salt, which was formed as a by-product in the reaction. The reaction mixture was dried by stripping a small portion of the solvent under vacuum. The solution, containing crude 1-hydroxycyclopentyl 2'-thienyl N-ethyl ketimine (96% pure by GC, area % analysis) in o-dichlorobenzene, was used, without isolation, for the thermal rearrangement reaction in Example 5.

Example 5

2-Ethylamine-2-(2'-thienyl)cyclohexanone
(tiletamine) Thermal Rearrangement Reaction A solution of crude 1-hydroxycyclopentyl 2'-thienyl N-ethyl ketimine (38.58 mmol assumed) in 25 mL of o-dichlorobenzene, from Example 4, was refluxed for 1.5 hours at 180° C. to synthesize 90% pure (GC, area % analysis) tiletamine free base, by thermal rearrangement.

Example 6

2-Ethylamino-2(2'-thienyl)cyclohexanone Hydrochloride (Tiletamine Hydrochloride)

a. o-Dichlorobenzene as a Solvent for the Acid Addition Salt Reaction

Hydrogen chloride gas (2.81 g, 77.16 mmol) was bubbled through a solution of tiletamine (38.58 mmol assumed—the mixture from Example 5) in o-dichlorobenzene, keeping the temperature at about 2° C. The resulting reaction mixture was filtered to produce 3.6 grams of a yellow solid. This solid was vigorously stirred for 30 min in 15 mL of acetone. The mixture was filtered, the solid reaction product was washed with acetone and dried at 40° C. giving 2.3 g of tiletamine hydrochloride (23% overall process yield through six steps, 99.93% pure by RP-IPC area % analysis). The filtrate and acetone wash were combined and subjected to evaporation to recover 4.47 g (36% corrected yield, 70% pure by GC area % analysis) of unreacted free tiletamine.

b. Di-n-butyl Ether as a Solvent for the Acid Addition Salt Reaction

Hydrogen chloride gas (2.81 g, 77.16 mmol) is bubbled through a solution of tiletamine (38.58 mmol assumed—the mixture from Example 5) in di-n-butyl ether, keeping the temperature at about 2° C. The resulting reaction mixture is filtered to produce about 8.0 grams of a yellow solid. This solid is vigorously stirred for 30 min in 30 mL of acetone. The mixture is filtered, to remove the solid reaction product, the reaction product is washed with acetone and dried at 40° C. giving about 7.0 g of tiletamine hydrochloride.

c. Di-n-butyl Ether as a Solvent for the Acid Addition Salt Reaction of Mixed Reactants Hydrogen chloride gas (2.81 g, 77.16 mmol) was bubbled through a solution of a 7:1 mixture (molar ratio) of tiletamine and 1-hydroxycyclopentyl 2'-thienyl N-ethyl ketimine in di-n-butyl ether, as might be a typical mixture from the thermal rearrangement reaction of 1-hydroxycyclopentyl 2'-thienyl N-ethyl ketimine (38.58 mmol assumed) (Scheme 9) carried out in di-n-butyl ether, at 5° C. The resulting solid was filtered, washed with di-n-butyl ether and stirred vigorously for 0.5 hour in acetone. The solid was filtered, washed with acetone and dried at 40° C. to afford 5.4 g (95% pure by HPLC, area % analysis, 51% overall process yield through six steps). The filtrate and washed solutions were combined and subjected to evaporation to recover 1.8 g (19% corrected yield, 92% pure by GC area % analysis) unreacted 1-hydroxycyclopentyl 2'-thienyl N-ethyl ketimine.

What is claimed is:

1. A method of reacting thiophene with an acid halide of cyclopentanecarboxylic acid to produce cyclopentyl 2-thienyl ketone comprising contacting the acid halide of cyclopentanecarboxylic acid with thiophene and a solvent in the presence of a non-tin-containing solid catalyst.

2. The method of claim 1, wherein the solid catalyst is selected from the group consisting of aluminum chloride, graphite, and mixtures thereof.

3. The method of claim 1, further including the step of forming the acid halide of cyclopentanecarboxylic acid, as an intermediate, by reacting cyclopentanecarboxylic acid with a thionyl halide.

4. The method of claim 3, wherein the cyclopentanecarboxylic acid is reacted with the thionyl halide, without a solvent.

5. The method of claim 3, wherein the cyclopentanecarboxylic acid is reacted with the thionyl halide, in a solvent.

6. The method of claim 5, wherein the thionyl halide is thionyl chloride.

7. The method of claim 6, wherein the solvent is dichlorobenzene.

8. The method of claim 5, wherein after the reaction of cyclopentanecarboxylic acid with the thionyl halide to form the acid halide of cyclopentanecarboxylic acid, thiophene and a solid catalyst for the thiophene reaction is added, without separation of the intermediate cyclopentanecarboxylic acid halide.

9. The method of claim 8, further including adding additional solvent for the thiophene reaction.

10. The method of claim 9, wherein the solvent added for the thiophene reaction is the same solvent added for the reaction of cyclopentanecarboxylic acid and the thionyl halide.

11. The method of claim 10, wherein the solvent is selected from the group consisting of chlorobenzene, dichlorobenzene, and mixtures thereof.

12. The method of claim 11, wherein the solvent is dichlorobenzene.

13. The method of claim 12, wherein the solvent is o-dichlorobenzene.

14. The method of claim 8, wherein the solid catalyst is selected from the group consisting of graphite, an aluminum chloride, and mixtures thereof.

15. The method of claim 1, further comprising forming a tiletamine free base from the cyclopentyl 2-thienyl ketone by sequentially (a) contacting the cyclopentyl 2-thienyl ketone with a halide in the presence of a solvent for the cyclopentyl 2-thienyl ketone to form a halogenated cyclopentane 2-thienyl ketone; (b) aminating the halogenated cyclopentane 2-thienyl ketone by reaction with an amine; and (c) subjecting the reaction product of step (b) to thermal rearrangement, in a suitable solvent, and at a sufficient temperature to form tiletamine free base.

16. The method of claim 15 wherein steps (a), (b), and (c) are carried out in the presence of the same solvent.

17. The method of claim 16, wherein the solvent is dichlorobenzene.

18. The method of claim 15 wherein step (b) is achieved by adding an amine to the reaction mixture resulting from step (a), without first separating the halogenated cyclopentane 2-thienyl ketone from the reaction mixture.

19. The method of claim 18, wherein the halogenated cyclopentane 2-thienyl ketone reacts with ethylamine to form 1-hydroxycyclopentyl 2'-thienyl N-ethyl ketimine.

20. The method of claim 18, wherein step (c) is achieved by heating the reaction mixture resulting from step (b) without first separating the reaction product from step (b) from the reaction mixture.

21. The method of claim 20, wherein heating at a temperature sufficient for thermal rearrangement is accomplished by refluxing the reaction mixture at a temperature sufficient to vaporize the solvent.

22. The method of claim 21, wherein the boiling point of the solvent used in the thermal rearrangement reaction is at least 100° C.

23. The method of claim 15, further including the step of making an acid addition salt from the tiletamine free base by reacting the tiletamine free base with gaseous hydrogen halide in the presence of a solvent for the tiletamine free base.

24. The method of claim 23, wherein the solvent for the tiletamine free base is selected from the group consisting of chlorobenzene, dichlorobenzene, di-n-butyl ether, t-butyl methyl ether, and mixtures thereof.

25. The method of claim 24, wherein the solvent for the tiletamine free base is dichlorobenzene.

26. The method of claim 25, wherein the solvent for the tiletamine free base is o-dichlorobenzene.

27. The method of claim 24, wherein the solvent for the tiletamine free base is selected from the group di-n-butyl ether, t-butyl methyl ether and mixtures thereof.

28. The method of claim 25, wherein the solvent for the tiletamine free base is di-n-butyl ether.

* * * * *